United States Patent [19]
Salazar et al.

[11] Patent Number: 5,362,234
[45] Date of Patent: Nov. 8, 1994

[54] SELF-DRILLING ENDOSTEAL HOLLOW-BASKET IMPLANT SYSTEM WITH SHOCK-ABSORBER

[76] Inventors: Alfred Salazar, 17406 S. 92 E. Ave., Bixby, Okla. 74008; Ricardo Guerra, 4455 N. Newcastle, Hardwood Heights, Ill. 60656

[21] Appl. No.: 124,825
[22] Filed: Sep. 21, 1993
[51] Int. Cl.⁵ ............................................. A61C 13/28
[52] U.S. Cl. ................................... 433/169; 433/173
[58] Field of Search ............... 433/169, 173, 174, 175, 433/176

[56] References Cited
U.S. PATENT DOCUMENTS

| | | | |
|---|---|---|---|
| 3,955,280 | 5/1976 | Sneer | 433/169 |
| 4,713,003 | 12/1987 | Symington et al. | 433/173 |
| 4,960,381 | 10/1990 | Niznick | 433/174 |
| 5,145,371 | 9/1992 | Jorneus | 433/174 |

Primary Examiner—Cary E. O'Connor
Attorney, Agent, or Firm—Veo Peoples, Jr.

[57] ABSTRACT

This invention consists of three main parts and a shock-absorbing resilient member. The first main part is a self-drilling implant. The self-drilling implant is tubular in design, having a hollow basket that saves some of the bone granulate from the osteotomy. The bone granulate encourages the formation of a blood clot, helps to immobilize the implant and provides an absorbable substance to precipitate recalcification. The second part is a tissue extension that screws into the implant. The tissue extension has a socket which receives the third element, i.e., the keeper. Two alternative keeper designs, each with its own type of shock-absorbing member, are disclosed. Each keeper embodiment has a bi-frustum principle shape and a longitudinal central shaft. Various dental prosthesis may be attached to the keeper.

5 Claims, 6 Drawing Sheets

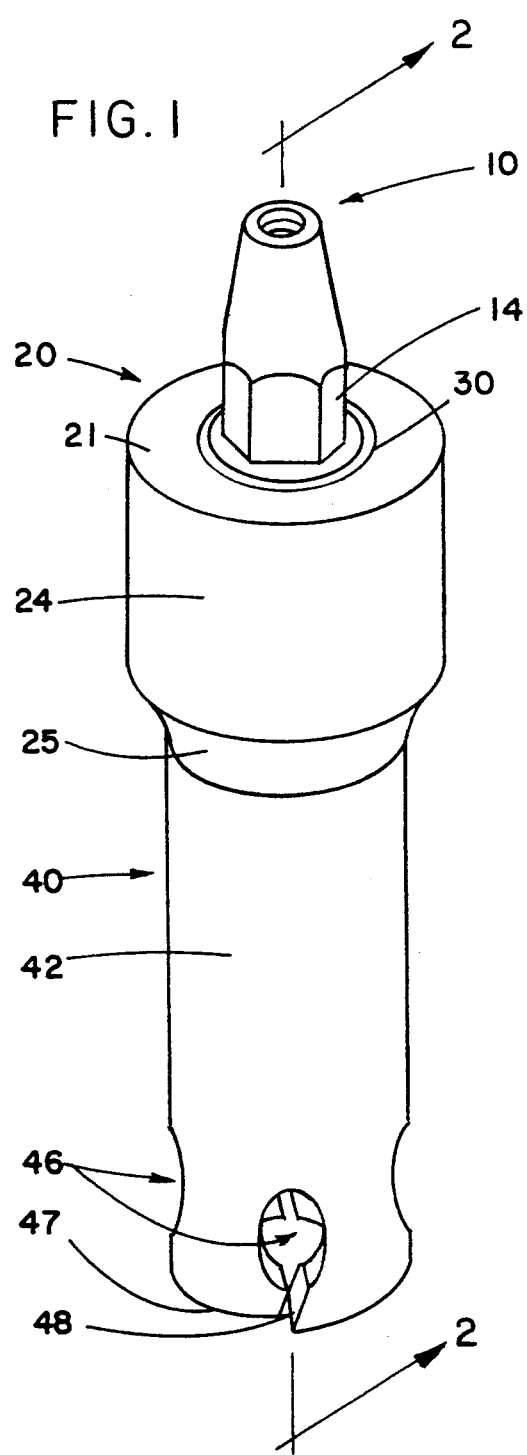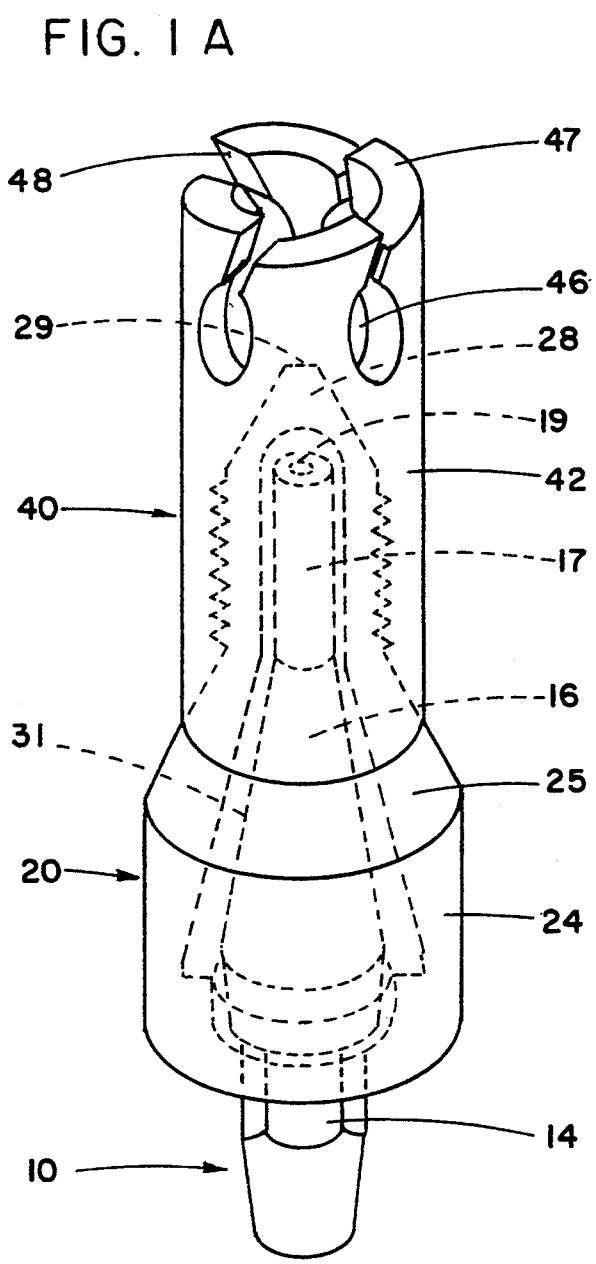

FIG. 2
FIG. 3
FIG. 4
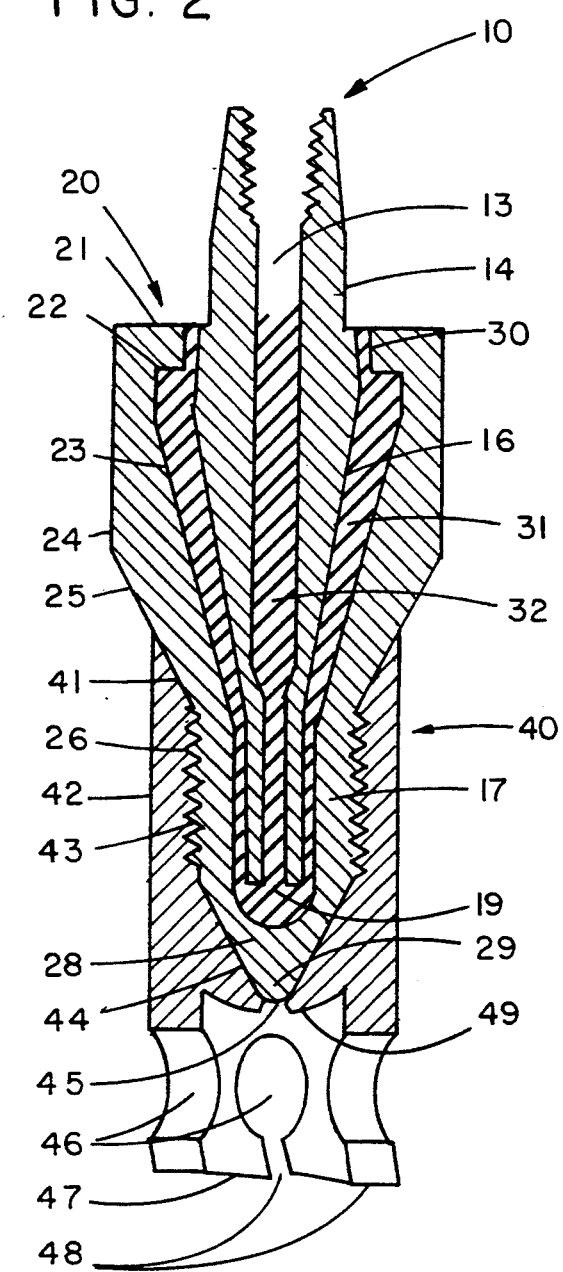
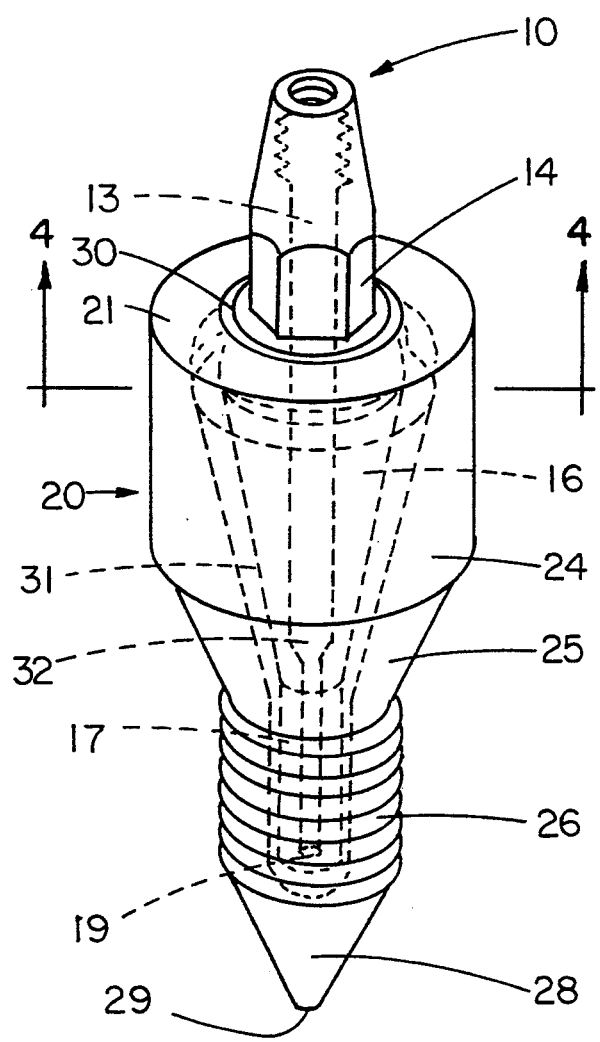
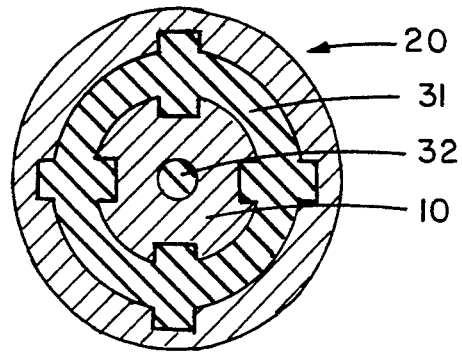

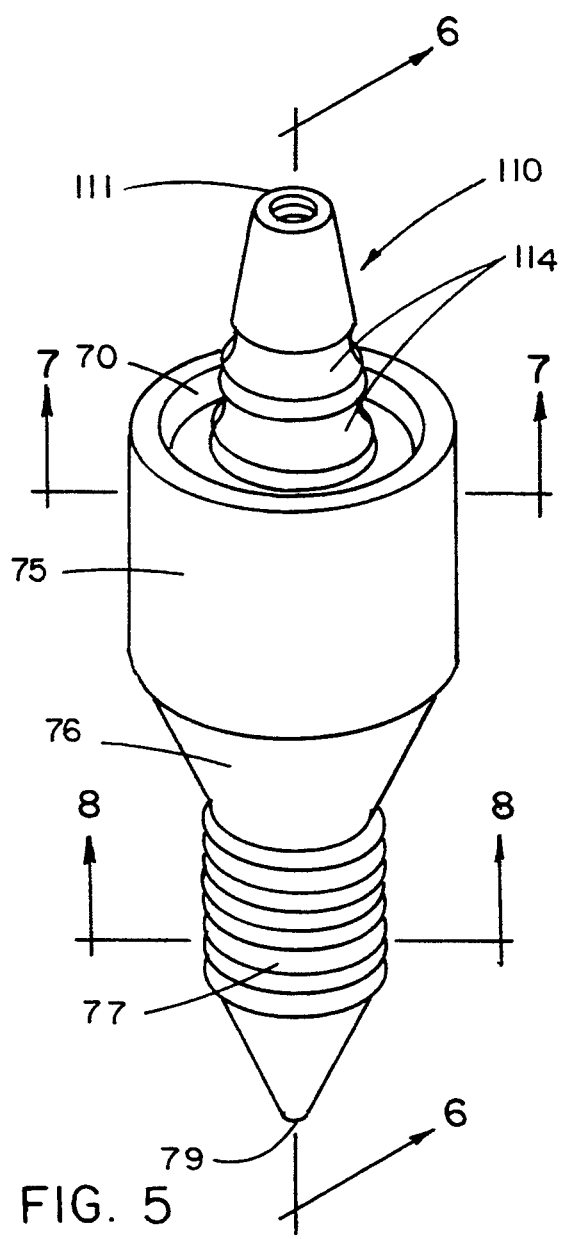
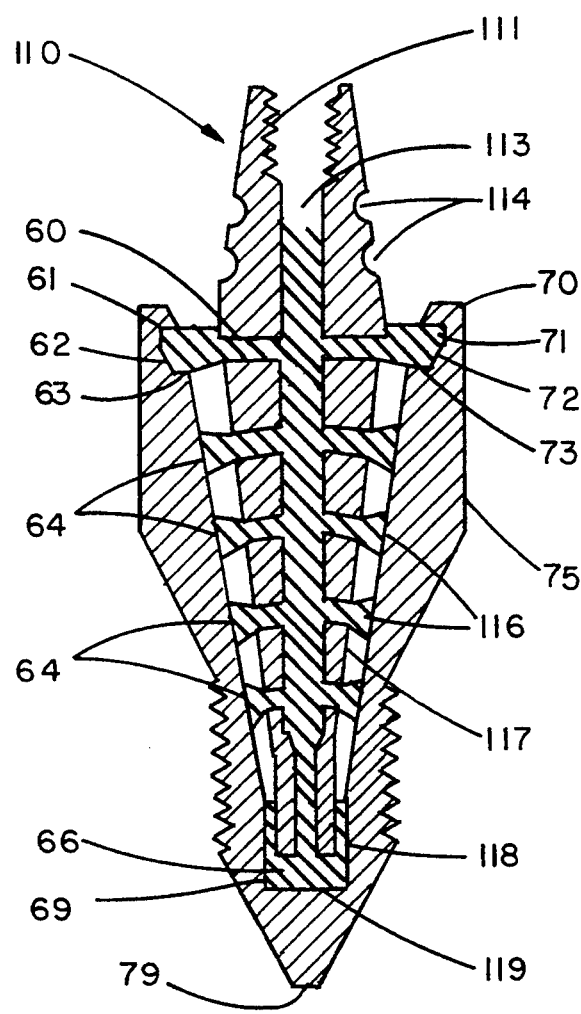
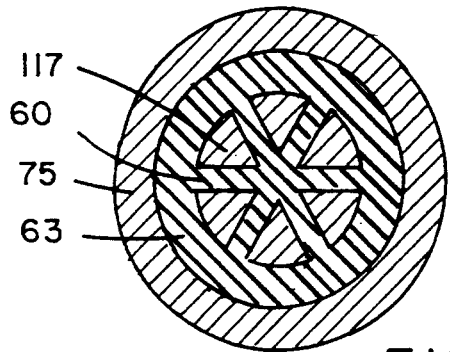
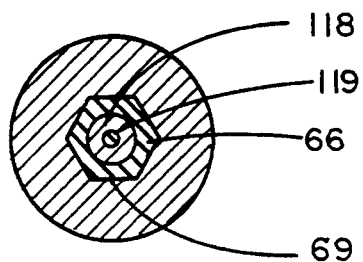

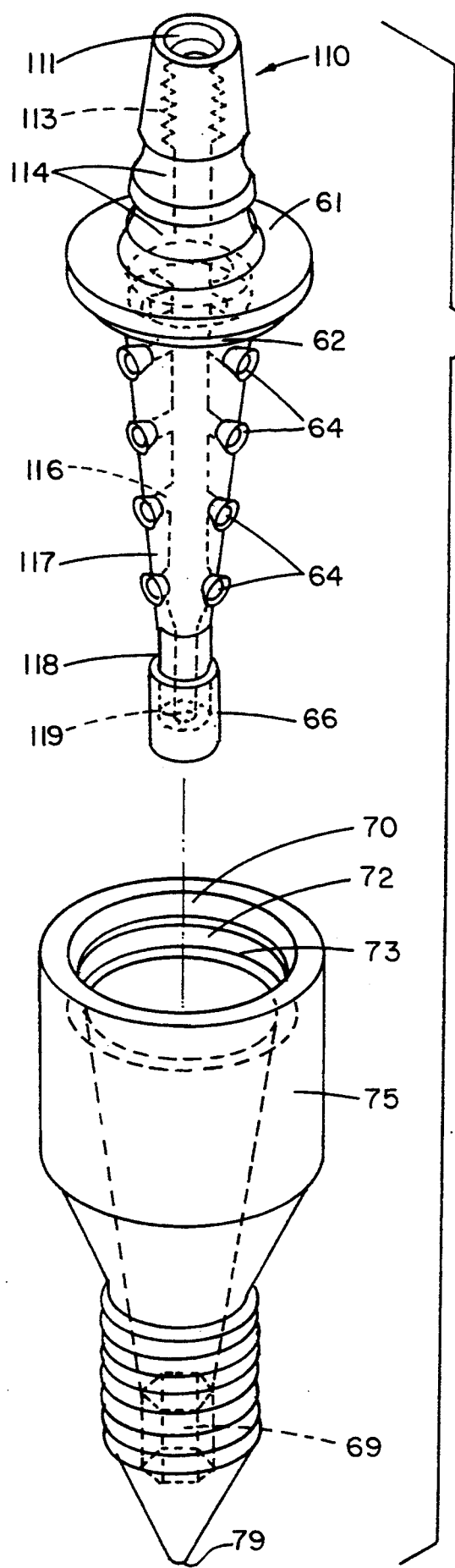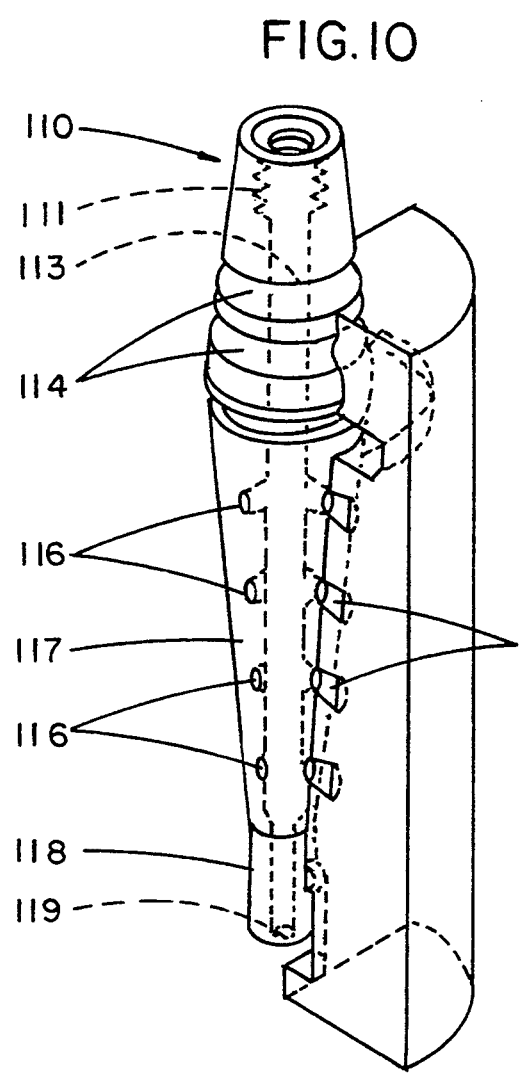

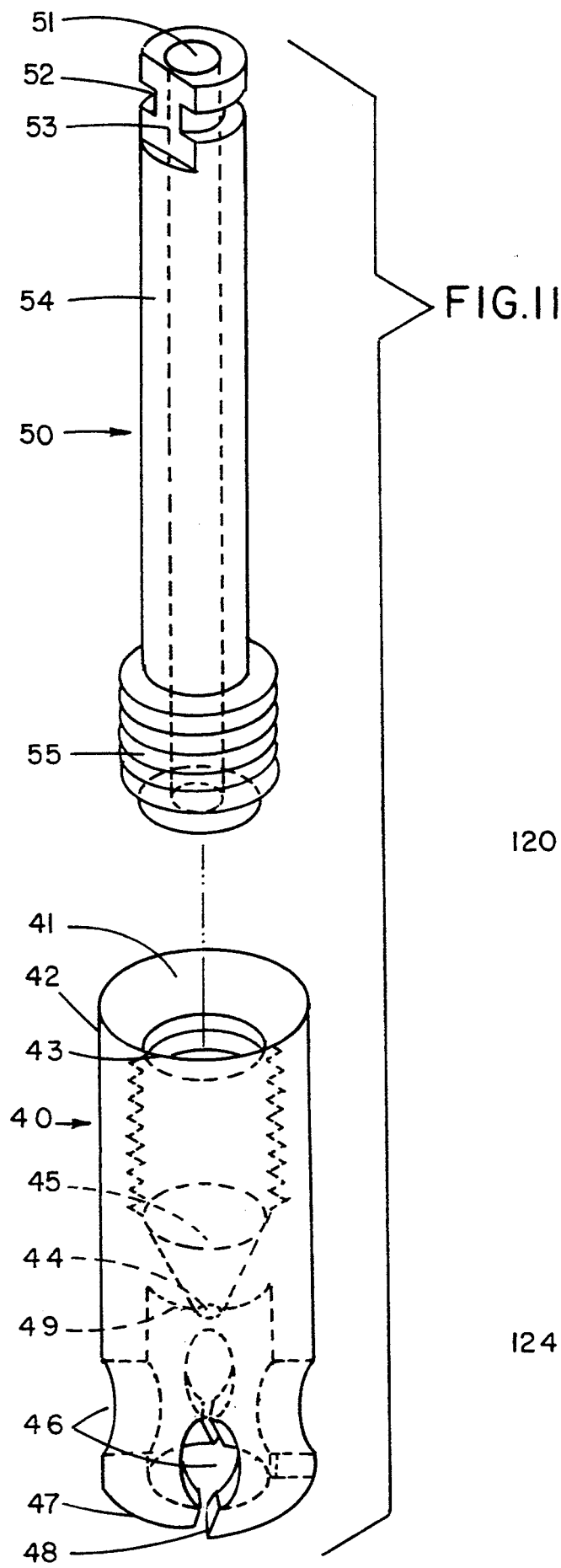
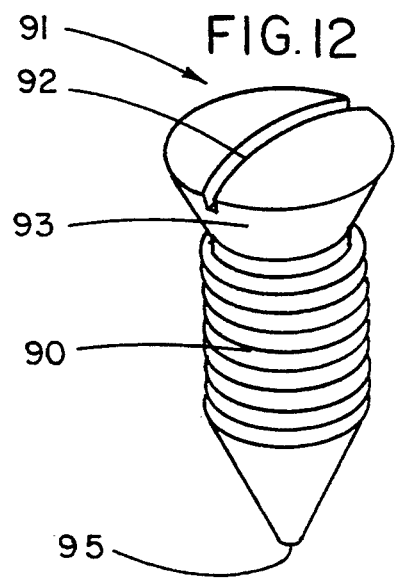
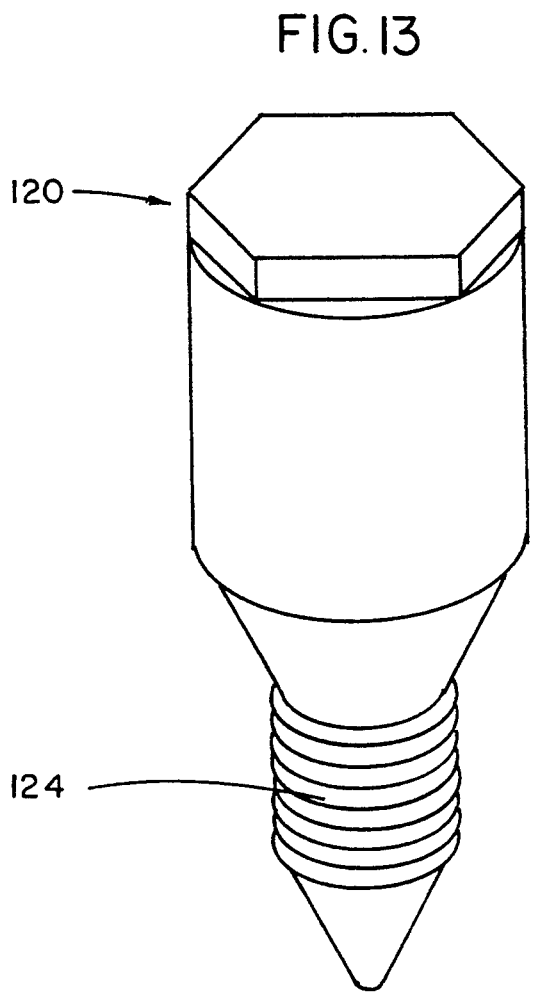

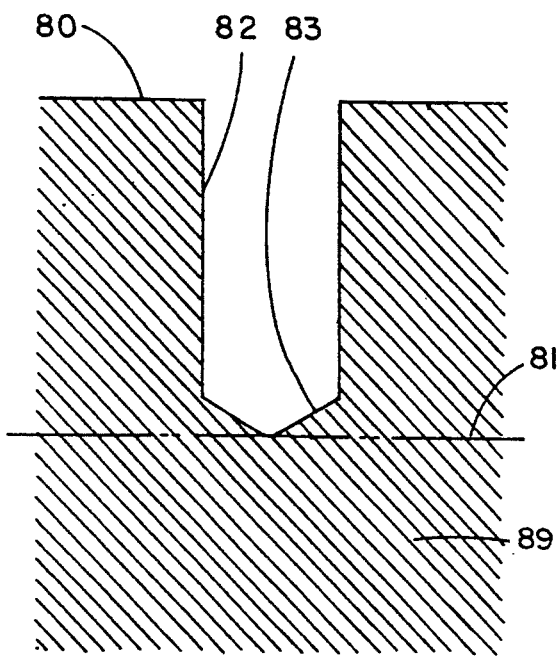
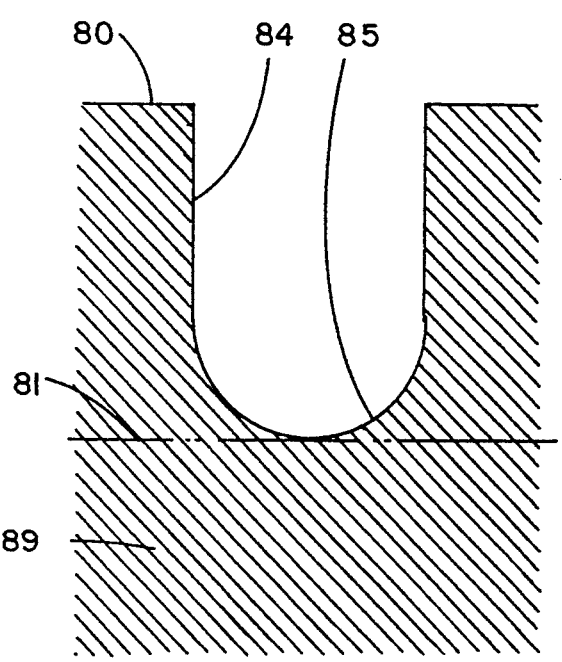
FIG.14A
FIG.14B
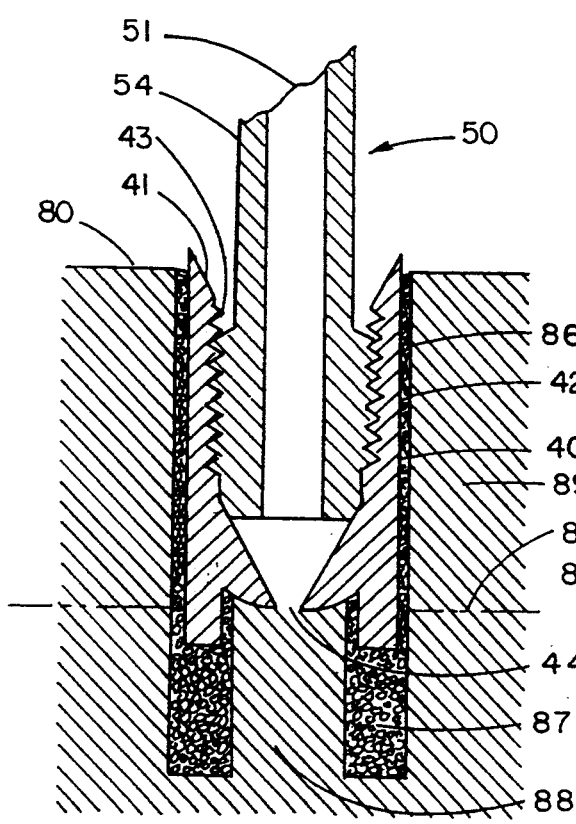
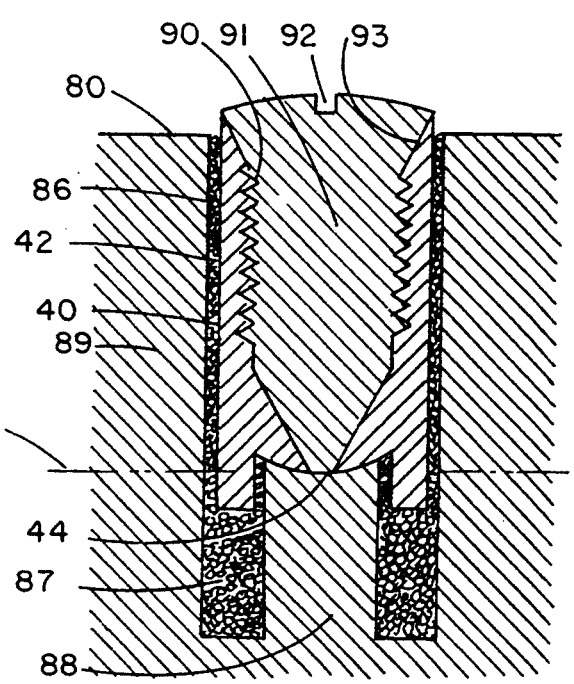
FIG.14C
FIG.14D

SELF-DRILLING ENDOSTEAL HOLLOW-BASKET IMPLANT SYSTEM WITH SHOCK-ABSORBER

BACKGROUND OF THE INVENTION

1. Field of the Invention

The present invention relates to an endosteal root-form dental implant system. More specifically, this invention relates to a self-drilling endosteal hollow-basket implant system with a tissue extension (sometimes referred to as a transmucosal abutment member) that supports and holds a keeper with shock-absorbing resilient means. Inserted onto the keeper may be various dental prosthesis designs.

2. Brief Description of the Prior

It is beyond the scope of this brief description to review the early attempts of men to replace missing teeth. Studies of Egyptian mummies from the middle kingdom up to Ptolomy's time revealed different processes of implantation.

A scientific breakthrough in the area of dental implants was achieved by Swedish Professor Per-Ingvar Branemark and co-workers. Combining a two-stage surgical technique with the use of titanium fixtures, these scientists achieved predictable results in surgical placement of permanent dental implants. Their continued studies in the early 1960's provided the basis of modern implantology.

However, because of the lack of periodontal ligaments between the bone and the titanium fixture, the implant lacked the natural motion and shock-absorbing capability of natural teeth.

Screw attachments have been employed between bone and fixture but under great stress they tend to fracture. In a publication titled "Dental Implant Prosthodontics" (J. B. Lippincott Company 1991 ISBN 0-397-51045-4), Ronald P. Desjardeins observed "The most common prosthesis problem that the author has thus far noted is the loosening or breakage of the gold locking screw with the resultant loosening of the prosthesis."

In the early 1970's, Dr. Kirsch from Germany designed an implant system called IMZ with a plastic shock-absorber called the IME. This device provides similar elastic properties as a periodontal ligament. The IME, which is a threaded intermediary sleeve, is installed inside of the implant by screwing it into the threaded bore of the implant. The sleeve has a threaded bore, into which a prosthesis is screwed.

However, in the same publication mentioned above, Robert J. Chapman observed that "the IME must be replaced every year or two, because it is plastic and will deteriorate somewhat with function."

That deterioration of the plastic sleeve opens a way for bacteria and changes the mechanical characteristics of this device. U.S. Pat. No. 4,622,010 describes a similar device that avoids the threads on the plastic sleeve.

U.S. Pat. No. 4,993,950 describes a keeper system which uses an O-ring "to permit universal 'rocking' motion of the keeper member relative to the true transmucosal cuff."

U.S. Pat. No. 5,006,068 describes a dental implant system with resilient force dampening means on the prothesis itself.

These designs provide a single means of shock-absorbing capacity and do not imitate the longitudinal movement of natural teeth. Other implant systems fail to mirror the movement of natural teeth. Such systems may feel unnatural to the person using such prior art dental implant systems. Furthermore, when a prosthesis is cemented to a natural tooth abutment and an implant abutment, the cement will be placed under great torquing stress to both ends of the prosthesis. This torquing stress may break the cement and cause the failure of the prosthesis.

Hollow-basket implants have advantages over the cylinder type. First, they require a minimum of bone removal that results in a less traumatic osteotomy. Second, they provide maximum anchoring surface and adequate mechanical strength. Because of its tubular shape with various perforations, it is able to withstand tension, compression or shearing stress and torque. The hollow-basket design also allows a two-sided growing of the bone tissue through the vents of the implant. Examples of prior art efforts are shown in one or more of the following U.S. Patents: U.S. Pat. No. 4,431,416; U.S. Pat. No. 4,951,819; U.S. Pat. No. 4,960,381; U.S. Pat. No. 4,842,517; U.S. Pat. No. 4,379,694; U.S. Pat. No. 4,657,510.

However, these prior art hollow-basket implants are not self-drilling. The insertion of prior art dental implant system involves a two-step surgical procedure. This is typical of endosteal root-form implant and is well known in the previous art. For the purpose of illustration, however, we are going to summarize the events of the two steps. First, the surgeon cuts a flap on the mucosa and drills a socket on the bone where the implant is then placed with a cover screw. The soft tissue is repositioned and the implant site is closed to avoid any movement of the implant and to prevent infection. Later in the second step, after osseointegration is complete, the surgeon uncovers and removes the cover screw. The surgeon then installs a healing cap which is later replaced by a tissue extension. It is into the tissue extension that the restoration is installed. On occasion the restoration is attached to an intermediate device, located between the tissue extension and the restoration, which we have referred to as a keeper.

SUMMARY OF THE INVENTION

This invention relates to a dental implant system comprising an implant with self-drilling capabilities. The self-drilling implant of the present invention is tubular in shape and contains a basket socket and an internal threaded socket. The basket socket is defined by cutting tooth edges designed to finish the osteotomy sinking the implant into its definitive place. Circular openings between the cutting tooth edges of the basket socket are equally spaced around the circumference of one end of the implant and they define the spaces between the cutting teeth. Their function is to collect some of the bone chips from the osteotomy and to provide space for the bone to grow out of this external socket in order to provide additional support for the implant.

The capability of saving bone chips from the osteotomy is a very important one since these bone chips will encourage the formation of a blood clot, help to immobilize the implant, and provide an absorbable, autogenous substance to precipitate recalcification. A restriction between the basket and internal sockets has a circular opening which allows the circulation of a cooling fluid during the drilling operation and serves as an opening to provide medication.

The internal socket of the implant is located opposite of the basket socket and has internal threads and serves four purposes. First, it receives an auxiliary hollow threaded adapter or driver which makes it possible to drive the implant into the jawbone using a standard, low-speed, internally-irrigated handpiece. Second, it receives a cover screw which is used to seal the threaded socket of the implant and the central restriction, during the initial integration period, to prevent bone ingrowth. Third, it receives a healing cap, which is a temporary extension used to maintain the opening through the gum tissue following second stage surgery. Finally, it receive the tissue extension.

The tissue extension serves two purposes. First, it extends the length of the implant from bone level to the gum level. This length is different for different patients, and for that reason, the tissue extension is manufactured in different lengths. Second, it holds and supports the keeper.

The tissue extension has four outside sections. First, a frustum section which fills and seals the internal restriction which defines the two implant sockets. The second section is a threaded area which allows the tissue extension to be securely threaded to the threaded socket of the implant. The third section has a conical shape which extends out of the implant's socket, sealing the opening and relieving stress from the threaded area. The last area has a cylindrical shape with a diameter slightly larger than the diameter of the implant. On top of the cylindrical section, the tissue extension has a deep socket, and an internal shoulder at the opening of the socket in order to hold the root-part of the keeper which is encapsulated in a resilient member. Beyond the shoulder, the socket has a void that is conical in shape with longitudinal grooves to avoid the rotation of the resilient member. The socket ends with a cylindrical hollow core that finishes close to the bottom of the tissue extension.

The keeper has a bi-frustum shape with a central hollow core and a tubular extension on one end. The tubular extension and the first frustum section next to it are the root-area of the keeper. The tubular extension provides additional leverage to avoid a "rocking" motion of some prior art designs and encourages the longitudinal motion of natural teeth. The frustum section of the root-area has longitudinal grooves to avoid the rotation of the keeper in the shock-absorbing member. The outside dimensions of the root-area of the keeper are smaller than the inside dimensions of the tissue extension's socket, leaving an empty space between both parts which is going to be filled by the resilient member. The last section of the keeper is the tooth stump which exits the tissue extension into the oral cavity in order to support, by different means, a variety of prostheses. This might include crowns, bridges, overdentures, et cetera. The tooth stump has a frustum shape with a hexagonal section in the central area. This hexagonal section serves two purposes: first, it receives an instrument to securely thread the tissue extension into the implant; and second, it avoids the rotation of the restoration on the keeper. The hollow core of the keeper has internal threads in the stump area to receive a screw. The restoration is attached to the stump by that screw, it can be cemented, or a combination of both.

With the root-area of the keeper in a concentric position, inside of the tissue extension's socket, a high quality silicone rubber-like compound is injected, as a fluid, to fill the space between both parts After "curing" this elastic resilient member, which completely encapsulates the root-area of the keeper, has a large surface area in intimate contact with the tissue extension's socket and the root-area of the keeper itself. This provides a shock-absorbing means for compression, shearing, torque, and tension stress; allowing for a limited movement of the keeper similar to the movement of natural teeth. Using different silicone rubber compounds and different pressures of injection, the resilience of the resilient member can be "tuned" to obtain differential elasticity. This is an important feature of the present invention, since dependent upon the location of a tooth in the oral cavity, the teeth function under varying occlusal pressures.

For practical purposes, the tissue extension, the resilient member, and the keeper can be considered a single unit, since the internal shoulder at the opening of the tissue extension holds the elastic resilient member in its place which in turn holds the keeper. However, if an extreme frontal force, as in an accident, hits the restoration thereby endangering the integrity of the jawbone, the keeper will exit the tissue extension as natural teeth do to avoid further damage to the Jawbone.

Presently, there is also a second preferred embodiment of the tissue extension-resilient member-keeper assembly, and it is going to be described thusly:

The outside shape of the tissue extension of the second preferred embodiment has the same characteristics of the outside shape of the tissue extension of the first preferred embodiment; however, the socket has three differences. First, the internal shoulder becomes a groove which is going to hold an elastomeric seal. Second, the grooves of the void conical area are eliminated. Third, the cylindrical hollow core at the end of the socket is changed into a hexagonal socket which will serve two purposes. First, it is going to receive an Allen wrench to securely thread the tissue extension to the implant; secondly, it is going to receive the tubular extension of the keeper.

The overall shape of the keeper of the second preferred embodiment is similar to the shape of the keeper of the first preferred embodiment except in two details. First, the frustum section of the root-area does not have grooves but has many holes at different levels all around its circumference, which are connected to the central core. Second, it has a transverse groove all around its circumference to hold the seal where the keeper exits the tissue extension. The groove also is connected to the central core of the keeper. The tooth stump of the second preferred embodiment has the same shape as the tooth stump of the first preferred embodiment, except that the hexagonal section is not necessary since the tissue extension itself has a hexagonal socket as mentioned above.

The shock-absorbing resilient member of the second preferred embodiment differs substantially from the shock-absorbing resilient member of the first preferred embodiment. The shock-absorbing member of the second embodiment has three well-defined features. The first element is a boot that covers the extension on the root-area of the keeper. This boot isolates and holds in a concentric position the extension, respective to the socket, of the tissue extension. The second element consists essentially of many suction cups all around and at different levels of the frustum on the root-area of the keeper. These suction cups are tension and compression shock-absorbers, working as the periodontal ligament does. The last element is a seal positioned on the transverse groove of the keeper where the keeper exits the tissue extension. This seal closes the opening of the tissue extension's socket, thus preventing any foreign substance entrance. The seal is going to have a hexagonal section, and the groove of the tissue extension will have an internal hexagonal section to prevent the rotation of the keeper in those particular cases that rotation should be avoided, as in a single tooth restoration. However, when more than one implant are going to hold a restoration, the seal and the groove in the tissue extension will have a circular section, which is easy to manufacture, since rotation of the keeper is not a problem in these cases. All these elements of the shock-absorbing member are formed in a single operation by injecting the silicone rubber-like compound, as a fluid under pressure, through the central core of the keeper, which is in a multi-part mold.

The keeper of the second preferred embodiment can be removed by the patient for purposes of personal hygiene, allowing the use of a Water Pik (or similar deep cleaning device) to clean the socket of the tissue extension. The keeper of the second preferred embodiment has the same safety feature as the keeper of the first preferred embodiment. Both are designed to exit the tissue extension in the event of an extreme frontal impact that may put in jeopardy the integrity of the jaw bone.

An object of the present invention is to provide a dental implant system which is able to relieve the prosthesis if stricken by excessive frontal force, avoiding damage to the jawbone.

A principle object of the present invention is to provide a self-drilling implant that saves the bone granulate from the final stages of the drilling step. This provides several advantages. First, a scaffold to facilitate blood clotting is formed. Second, the bone granulates provide a physical means to immobilize the implant in its socket. Finally, the bone granulates provide an absorbable matter not foreign to the patient.

An additional object of the present invention is to provide an implant system which mimics the shock-absorbing capabilities of natural teeth.

Another object of the present invention is to provide an implant system which mimics the longitudinal movement of natural teeth.

A further object of the present invention is to provide an implant system that is easy to clean by the patient without the necessity of a dental visit.

BRIEF DESCRIPTION OF THE DRAWINGS

The invention will be more fully comprehended when considered with reference to the accompanying drawings and the explanations thereof.

FIG. 1 is a perspective view of the first preferred embodiment of the dental implant system of the present invention.

FIG. 1A is a bottom perspective view of the first preferred embodiment of the dental implant system of the present invention.

FIG. 2 is a section view of the first preferred embodiment taken along line 2—2 of FIG. 1.

FIG. 3 is a perspective view of the first preferred embodiment keeper affixed inside the tissue extension.

FIG. 4 is a sectional view of the first preferred embodiment taken along line 4—4 of FIG. 3.

FIG. 5 is a perspective view of the tissue extension with the second preferred embodiment of the keeper affixed inside.

FIG. 6 is a sectional view of the second preferred embodiment keeper and tissue extension taken along line 6—6 of FIG. 5.

FIG. 7 is a sectional view of the second preferred embodiment keeper and tissue extension taken along line 7—7 of FIG. 5.

FIG. 8 is a sectional view of the second preferred embodiment keeper and tissue extension taken along line 8—8 of FIG. 5.

FIG. 9 is a perspective view of the second preferred embodiment of the keeper and the tissue extension disassembled.

FIG. 10 is a perspective cut-away view of the mold that is used to form the second preferred embodiment of the keeper.

FIG. 11 is a perspective view of the driver and implant before the adaptor is inserted into the implant.

FIG. 12 is a perspective view of the cover screw.

FIG. 13 is a perspective view of the healing cap.

FIG. 14 shows four different sectional views of the drilling procedure accomplished during the first surgical stage. "A" is a view of the pilot osteotomy made with a pilot drill (drill not shown). "B" is a view of the second stage osteotomy made with a blade drill (drill not shown). "C" is a view of the implant fixture driven to its final placement showing a section of the driver shaft in place. "D" is a view of the implants' fixture after replacing the driver shaft with the cover screw.

DETAILED DESCRIPTION AND PREFERRED EMBODIMENTS

FIG. 1 and FIG. 1A illustrate a fully assembled dental implant system of the present invention which can be implanted in the upper or lower jaw. The fully implanted system consists of three main elements and a shock-absorbing member. The three main parts are: the implant 40, the tissue extension 20 and the keeper 10. These parts are made of material with chemical, physical and biological characteristics adapted for implantation in the oral cavity. Commercially pure titanium and certain medical grade titanium alloys are preferred for the implant 40, the tissue extension 20 and the keeper 10. The shock-absorbing member 30 is made of a high quality silicone rubber-like compound.

Three auxiliary parts help the implantation process during the two-stage surgical procedure. The three auxiliary parts are the adapter driver 50, the cover screw 90 and the healing cap 130. These three auxiliary parts are made of the same material as the three main elements to avoid galvanism, and will be explained later in this description.

The self-drilling implant 40, shown in FIGS. 1, 1A, 2, 11, 14C and 14D has a tubular shape with internal surfaces 44 and 49 which define two sockets meeting at an orifice 45. This orifice 45 provides a passage for the cooling fluid during the drilling operation and serves as an opening for medication to fight local infection or pain. The first socket extends from wall 49 vertically to adjacent cutting tooth edges 47 which is almost horizontal and 48 which is approximately perpendicular thereto. They are adapted to finish the osteotomy by sinking the implant to its definitive place. The cutting teeth are defined by this inclined lip surface 47, the nearly vertical surface 48, and the openings 46 between the teeth. While this is similar to a surgical trephine bur, the preferred embodiment of the implant of the present invention has several new features. First, it has fewer teeth since it only works in the spongiosa 89, which is a less dense section of bone. Also, the lip surface 47 has a minor inclination angle to provide better support after osseointegration. Each tooth or cutting edge 48, of the implant 40, is spaced apart by a definitive collecting hole 46 where most of the bone granulate produced during the drilling are collected.

To avoid overheating and provide space between the implant and the bone socket, a clearance 86 is provided by the alternate bending of the implant teeth or by increasing the width at the edge 47 of the teeth 48. Circular openings 46 between the teeth of the first socket have their outside periphery defined by the cylindrical surface 42 which as seen in FIG. 1 defines the lower portion of the implant. The function of these openings 46 and the first socket is to save some of the bone chips 87 (at FIGS. 14C and D) from the osteotomy and to provide a space within which the bone from both sides 88 and 89 (FIGS. 14C and D) of the bone socket can grow to support and anchor the implant.

The surface 49 of the first socket is convex in order to seat the concave surface 85 of the bone socket, shown in FIG. 14B, of the osteotomy.

The second socket of the implant as shown in FIG. 2 is angled and sloped at surface 41 extending above the internal threads 43 to provide a sealing surface and relieve compression and shearing stress from the threaded area 43.

The internal threads 43 serve four purposes: first, to secure the driver 50 during the self-drilling operation; second, to secure the cover screw 90 on the first surgical stage; third, to secure the healing cap 130 in the second surgical stage; and, finally, to secure either tissue extension 20 or 70 after healing of the soft tissue is completed.

The outside surface 42 of the implant 40 may be textured or a coating of a bio-compatible compound such as hydroxyapatite or titanium plasma may be sprayed on it to increase the surface area and allow bone ingrowth.

This orifice 45 will be closed by the cover screw 90 in the first stage of surgery and later by the lower portion 136 of the healing cap 130 and finally by the lower portion 29 of the tissue extension 20 or 79 for extension 70 to isolate the bone. This prevents ingrowth of the bone tissue from the first socket to the interior of the implant.

The present invention improves the multiple step drilling operation for endosteal root-form implants that use continuous irrigation by a cooling fluid. The process of this invention begins by drilling a pilot hole defined by 82 and 83 in the jawbone 80 for the osteotomy as shown in FIG. 14A. It is possible to insert a parallel pin (not shown) to check proper angularity. In step two, as shown in FIG. 14B, a bigger drill is driven to line 81 correcting any minor error of parallelism. The diameter of this drill is similar to the implant's diameter. In step three, FIG. 14C, the procedure differs substantially from the prior art, in that the implant itself, rather than an extraneous drill bit, is driven by the driver 50 shown in FIG. 11 and FIG. 14C finishing the osteotomy.

Referring to FIG. 11, this driver 50 has a hollow core 51 to deliver the cooling fluid irrigation during the drilling procedure. A groove 52 and a cutout section 53 in the shaft allow the use of a standard handpiece (not shown). The outside diameter of the shaft 54 can be increased substantially to reduce vibration. The threads 55 at the end of the driver 50 are manufactured with enough clearance to facilitate the unscrewing of the driver 50 from the implant 40 without removing the fixture from the bone socket defined by 84 and 85 in FIG. 14B. The driver 50 is intended to be pre-installed in the implant 40 to facilitate handling. This reduces surgical time and avoids contamination.

A portion of the bone granulate is moved, by the cooling fluid, to positions (FIGS. 14C and 14D) within the clearance 86 between the implant outer surface 42 and bone socket 84.

The bone granulate in the clearance 86 between the implant fixture 40 and the bone socket 84 and the bone granulate 87 in the collecting holes 46 encourage the formation of capillary blood vessels and new bone tissue with a laminar structure.

The technique for driving the implant differs from prior art techniques which recommend that "Profuse internal irrigation is required to keep the drill from clogging" and which recommend to ". . . clean drill head often to remove debris and ensure a sharp cutting surface." That is, the self-drilling implant of the present invention does not require a profuse internal irrigation to keep the drill from clogging since the implant is itself the drill. The debris need not be removed to ensure sharp cutting because collecting holes 46 serve to receive and disperse the bone granulate into clearance 86. The irrigation needed for the implant of the present invention is merely that required for cooling purposes only and may be kept at a minimum volume using a previously refrigerated cooling fluid. This characteristic saves in evacuation and helps reduce the amount of cooling fluid used.

The preferred embodiment of the implant fixture 40 does not have to be cleaned of debris to ensure a sharp cutting surface. One reason is that the self-drilling implant 40 is going to finish the osteotomy of only one socket. Regular drills usually make twenty-five sockets. Thus, the process of the present invention assures a perfectly sharp cutting edge every time and saves the time of having to "clean the head often".

Those skilled in the art can appreciate that one of the most important features of the present invention is that it saves bone granulate from the final drilling stage. As previously stated, this has three advantages. First, it provides a scaffold for formation of a blood clot. Secondly, it provides a physical means to help immobilize the fixture in the socket. Finally, it provides an absorbable substance not foreign to the patient.

For purpose of illustration, FIGS. 14C and 14D show the bone granulate 87 in the collecting holes 46 and throughout the clearance 86. They also show the bone core 88 that remains inside the drilling cavity defined by the inner surface of teeth 48. This core 88 remains attached to the bone and provides support and blood irrigation. During osseointegration, the bone core 88 is going to grow through the collecting holes 46 providing additional support and anchorage to hold the fixture in place.

If desired, additional rows of collecting holes 46 can be added. To finish the osteotomy the surgeon reverses the handpiece rotation to remove the adaptor 50 without disturbing the self-drilling implant 40, and install the cover screw 90.

The cover screw 40 of the present invention FIG. 12 and FIG. 14d has a slot 92 in its conical head 93 to allow the use of a screwdriver. External threads 91 engage the internal threads 43 of the implant 40. The lower end has a conical shape 92 and a circular tip 95 which closes the opening 45 between the two sockets. The function of the screw 90 is to seal the coronal opening 41 of the implant 40 and seal the opening 45 between the two sockets to avoid the growth of bone over the implant.

In the second surgical stage, after osseointegration has been achieved, the cover screw 90 is uncovered and replaced with the healing cap as shown in FIG. 13 to maintain the opening through the tissue and cover the orifice 45 in the implant 40 socket defined by 41, 43 and 44.

The lower end of the healing cap 133-136 is similar in shape and dimensions to the cover screw 90 since both are designed to screw into the implant internal socket 41; however, the healing cap 130 has a cylindrical extension 132 which maintains the opening through the tissue following second stage surgery. The hexagonal head 131 of the healing cap 130 allowed the use of a hexagonal instrument (not shown) for its installation and removal after the healing of the tissue when it is replaced with the tissue extension 20 or 70. The tissue extension 20 or 70 is inserted into the implant fixture 40. The tissue extension 20 or 70 holds the keeper 10 or 110, respectively.

The first preferred embodiment of the tissue extension 20 (FIGS. 2 and 3) of the present invention has a highly polished intramucosal surface 24 and a highly polished surface 21 to the oral cavity which better control plaque. External threads 26 securely hold the tissue extension 20 to the internal threads 43 of the implant fixture 40. A conical section 25 extending above the threads 26 provides an airtight stop, which seals or locks the extension 20 and protects the threaded area 26 from compression and shearing stress. A second conical section 28 extending below the threads 26 performs the same function but also serves as a closure for fixture orifice opening 45. The inside section 23 of the extension 20 defines the hollow interior of 20. Section 23 can be polygonal shaped at its lower end 69 seen in FIG. 9, when the implant is designed for single tooth prosthesis. This shape avoids rotation of the keeper end 66 which would also be polygonal. However, when the tissue extension 20 is intended for a bridge or overdenture, this lower end section 69 can be cylindrical with a cylindrical end 66 for the keeper, since torsion is not a problem in bridge or overdenture prothesis.

FIGS. 2 and 3 show the first preferred embodiment of the keeper 10 assembled within the tissue extension 20. The keeper 10 and tissue extension 20 function as a single unit in this embodiment. A resilient compound such as silicone rubber is injected in a fluid state through the main shaft 13 of the keeper 10 to form a coating 30, 31 which is in the form of a cocoon in intimate contact with the keeper 10 and tissue extension 20.

The FIGS. 2 and 3 show the keeper 10, at its proximal end 11 through 14, is designed to support a variety of dental prostheses. Its main shaft 13 opens at its distal end 19, through which the injected silicone rubber compound 32 exits and coats the keeper exterior surfaces 30 and 31.

A shoulder 22 underneath the surface 21 on the tissue extension 20 holds and conforms the resilient silicone compound 30 to surround the body portion 16 of the keeper 10.

This configuration of the resilient compound acts as a shock-absorber able to control compression, shearing and tensile stresses applied over the keeper 10 imitating the shock-absorbing characteristics and movement of natural teeth. For instance, depending on the location in the oral cavity, the textural composition of the silicone compound will vary from soft for frontal teeth prosthesis and progress to medium and hard for molar prosthesis. This characteristic is very desirable and has been attempted many times in the prior art with varying degrees of success.

The first preferred embodiment keeper 10 design of the present invention facilitates ease of manufacture. That is, since the encapsulated keeper 16, 17 is not in direct contact with the tissue extension 20, broader tolerances during manufacturing are allowed. Minor variations in width of the keeper 10 can be compensated for by the resilient silicone rubber at 30 and 31.

This first preferred keeper design 10 also facilitates ease of maintenance. The resilient silicone rubber 32 is injected from the inner main shaft 13 which therefore displaces air while filling the voids. This produces an airtight seal that prevents the entrance of bacteria, saliva, or food after the silicone rubber sets.

The first embodiment keeper of the present invention 10 incorporates two safety features to protect the integrity of the jawbone at 80 and 89. That is, if an extreme frontal force hits the prosthesis and endangers the integrity of the jawbone, that force will disengage the keeper from its silicone rubber at 30 and the keeper 10 would then be expelled from the tissue extension 20. The conical shape 16 of the keeper helps to promote this purpose. If an extreme frontal force hits the prosthesis, the keeper is going to break off at its narrower end thus protecting the jawbone from that force, assuming the keeper has not been expelled by the force. In either case, the keeper can be replaced as simply as an electric fuse can be replaced after an overload condition.

These safety features are distinct from and an improvement over the prior art.

In the second preferred embodiment of the keeper which is illustrated in FIGS. 5, 6, 7, 8, 9 and 10, the silicone resilient member 60 to 66 is also injected through the main shaft 113 of the keeper 110. FIG. 10 shows a section of the mold which surrounds the keeper 110 during injection. After the silicone rubber is cured in the mold, then the mold is removed. A base support 118 located below the lower end of the keeper 110 is formed by the silicone rubber as it exits the keeper 110 through the opening 119 located at the bottom end.

The keeper 110 has a plurality of shock-absorbing members 60-66 along the keeper periphery. A plurality of mini-suction cups 64 are among the shock-absorbing members. These suction cups 64 extend from all around the main body 117 of the keeper 110 at different levels. They are formed by the injection molding process described above and illustrated in FIG. 10. The resilient silicone rubber exits throughout the vents 116 along the outer surface of the keeper 110 to fill each of a plurality of cavities 124 in the mold where the suction cups 64 are formed. Collectively, the suction cups 64 function like the periodontal ligament of natural tooth absorbing tensile, compression and shearing stress from the masticatory forces.

Also among the shock-absorbing members is a seal 61 located at the keeper midsection to interface where the keeper 110 exits the tissue extension 70 above the cylinder 75. The seal 61 under-surface is beveled at section 62 to facilitate its introduction through the extension 70 opening. The tissue extension is further defined by grooves 71, 72 and 73 that engage and retain the elastic-resilient seal 61, and the keeper 110 in a central upright position.

The outside shape of the tissue extension 70 for the second preferred embodiment of the keeper 110 is similar to the outside shape of the tissue extension 20 for the first preferred embodiment. However, the second preferred embodiment extension 70 as illustrated differs on the inside in two ways. First, it has a hexagonal socket 69 at its lower inside that is designed for the use of an allen wrench to secure the abutment to a foundation fixture. That socket 69 later on is going to receive the keeper base support 66 which, although cylindrical in FIG. 9, can also be hexagonal. Second, it has grooves 71, 72 and 73 to hold the seal members 61, 62 and 63 in place.

The second preferred embodiment keeper 110 has the same safety features of the first preferred embodiment 10, but the keeper 110 of the second embodiment can be mechanically removed by the patient to perform thorough hygiene cleaning and self-inspection of the abutment's socket and the keeper-prosthesis itself. The keeper 110 is engaged by mechanical suction and engagement rather than by composition adhesion used for the keeper 10 of the first preferred embodiment.

This capability will enable the oral hygiene of the patient even though the socket is sealed from air.

The implant 40 of the second preferred embodiment is the same foundation fixture of the first preferred embodiment.

What is claimed is:

1. A self-drilling endosteal hollow-basket implant system with shock-absorber comprising:
   a. an implant fixture having an internal socket for receiving a tissue extension and having collection holes defining spaces between cutting teeth for drilling, and said teeth defining a hollow basket socket at the distal end of the implant; and
   b. a tissue extension, telescopically engageable into the internal socket of the implant fixture, said extension having an opening at one end which opens into a hollow interior cavity or socket for receiving a keeper; and
   c. a keep member to be inserted within the extension, said keeper member being selected from the group consisting of
      i. a keeper comprising a main central shaft extending throughout the length of the keeper and open at each end for receiving, collecting, and dispersing silicone rubber shock-absorbing fluid, and said keeper having an outer shape conforming to the hollow interior of the tissue extension but appreciably narrower than said hollow interior thus permitting said shock-absorbing fluid to be collected within said shaft and to be dispersed through that portion of the tissue extension hollow interior which remains unoccupied by said keeper; and
      ii. a keeper having an outer shape conforming to the hollow interior of the tissue extension except that said keeper further comprises a silicone rubber injection molded core, a network of silicone injection molded internal lateral ribs, and each rib having extended therefrom, at the outer surface of the keeper, silicone rubber injection molded suction cups which are releasably engageable from inside of the tissue extension; said keeper also comprising a seal member for closing the open end of the tissue extension upon insertion of the keeper therein.

2. An improved method for dental implantation comprising producing an osteotomy from the foundation fixture of claim 1 by a drilling action while accumulating and collecting jawbone granulates between the oral cavity formed by said drilling action and the fixture itself;
   whereby the need to frequently clean extraneous drill heads, remove bone granulate, and the need for profuse irrigation is negated.

3. The implant system of claim 1 wherein the hollow basket is convex.

4. The implant system of claim 1 wherein the outside surface is textured or coated by an a material selected from the group consisting of hydroxyapatite and titanium plasma.

5. The implant of claim 1 having a cover screw, a healing cap and an adapter driver which are screwable into the internal socket of the implant which receives the tissue extension.

* * * * *